United States Patent [19]
Pi Subirana et al.

[11] Patent Number: 6,008,391
[45] Date of Patent: Dec. 28, 1999

[54] PROCESS FOR PREPARING ALKOXYLATED FATTY ACID ALKYL ESTERS

[75] Inventors: Rafael Pi Subirana, Granollers; Joaquim Llosas Bigorra, Sabaadell, both of Spain

[73] Assignee: Henkel Kommanditgesellschaft auf Aktien, Duesseldorf, Germany

[21] Appl. No.: 09/155,372

[22] PCT Filed: Mar. 17, 1997

[86] PCT No.: PCT/EP97/01326

§ 371 Date: Sep. 25, 1998

§ 102(e) Date: Sep. 25, 1998

[87] PCT Pub. No.: WO97/35830

PCT Pub. Date: Oct. 2, 1997

[51] Int. Cl.[6] ............................ C07C 51/00
[52] U.S. Cl. ............................ 554/149; 554/148
[58] Field of Search ........................... 554/148, 149

[56] References Cited

U.S. PATENT DOCUMENTS 5,292,910  3/1994  Raths et al. ........................... 554/149

FOREIGN PATENT DOCUMENTS

| 0 523 089 | 1/1993 | European Pat. Off. . |
| 0 339 425 | 3/1994 | European Pat. Off. . |
| 0 619 291 | 10/1994 | European Pat. Off. . |
| 44 46 064 | 6/1995 | Germany . |

OTHER PUBLICATIONS

Weil. et al., J. Am. Oil. Chem. Soc., Sep., 1979, vol. 56, pp. 873–877.

Hama, et al., J. Am. Oil. Chem. Soc., AOCS Press (1995), vol. 72, No. 7, pp. 781–784.

*Primary Examiner*—Deborah D Carr
*Attorney, Agent, or Firm*—Ernest G. Szoke; Wayne C. Jaeschke; Steven J. Trzaska

[57] ABSTRACT

A process for making alkoxylated fatty acid alkyl esters involving: (a) providing a fatty acid alkyl ester; (b) providing an alkylene oxide component; (c) providing a catalyst component containing a mixture of: (i) a primary catalyst; and (ii) an alkylene glycol having from 2 to 6 carbon atoms; and (d) reacting (a)–(c) to make the alkoxylated fatty acid alkyl ester.

8 Claims, No Drawings

PROCESS FOR PREPARING ALKOXYLATED FATTY ACID ALKYL ESTERS

This application is a 371 of PCT/EP92/01326 filed Mar. 17, 1997.

BACKGROUND OF THE INVENTION

1. Field of the Invention

This invention relates to a process for the alkoxylation of fatty acid alkyl esters in the presence of a homogeneous catalyst/co-catalyst system.

2. Discussion of Related Art

Alkoxylated alkyl esters, preferably so-called methyl ester ethoxylates, are known nonionic surfactants which have recently acquired considerable interest by virtue of their excellent washing performance. Relevant reviews can be found, for example, in J. Am. Oil Chem. Soc. 56, 873 (1979) and in J. Am. Oil Chem. Soc. 72, 781 (1995).

The addition of alkylene oxides onto compounds containing acidic hydrogen atoms, preferably onto primary alcohols, can be carried out in the presence of various, generally alkaline catalysts. Typical examples are potassium hydroxide or sodium methylate, which are added in the form of alcoholic solutions, or heterogeneous layer compounds of the hydrotalcite type which are introduced into the reaction mixture in the form of solids. By contrast, the insertion of alkylene oxides into the carbonyl ester bond is far more difficult and can only be achieved using special catalysts.

The use of calcined or fatty-acid-modified hydrotalcites for the ethoxylation of fatty acid esters is known from EP-B1 0 339 425 and EP-B1 0 523 089 (Henkel). According to DE-A1 44 46 064 (Lion), the ethoxylation of methyl esters is carried out in the presence of mixed metal oxides which have been surface-modified with metal hydroxides or metal alkoxides. However, these processes have a number of disadvantages. The use of heterogeneous catalysts, i.e. catalysts which are insoluble in the reaction mixture, is technically more complicated because the solid cannot be introduced like a liquid through an automatic metering unit, but generally has to be scooped into the reactor by hand. Removal of the catalyst is also problematical because the catalyst particles are generally so fine that they can only be filtered through special filter candles. However, the catalyst cannot be left in the reaction mixture either because otherwise clouding and sedimentation can occur. From the performance point of view, the results obtained with heterogeneous catalysts are not always satisfactory either. Thus, although the reaction is generally very quick, the products obtained normally have hydroxyl values well below the theoretical value. As a result, products with undesirably high cloud points are obtained. However, since nonionic surfactants only develop optimal washing performance above their cloud point, there is a need for alkoxylated alkyl esters with as low a cloud point as possible.

Accordingly, the problem addressed by the present invention was to provide new catalysts for the alkoxylation of fatty acid alkyl esters which would be free from the disadvantages mentioned above and which, on the one hand, would dissolve in the reaction product and, on the other hand, would give products having improved hydroxyl values and lower cloud points.

DESCRIPTION OF THE INVENTION

The present invention relates to a process for the production of alkoxylated fatty acid alkyl esters corresponding to formula (I):

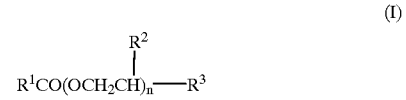

where $R^1CO$ is a linear or branched acyl group containing 6 to 22 carbon atoms and 0 and/or 1, 2 or 3 double bonds, $R^2$ is hydrogen or a methyl group, $R^3$ is a linear or branched alkyl group containing 1 to 22 carbon atoms and n is a number of—on average—1 to 20,
in which mixtures of
(a) alkali metal and/or alkaline earth metal hydroxides and/or alcoholates and
(b) alkylene glycols
are used as catalysts.

Whereas alkali metal hydroxides on their own do not catalyze the alkoxylation of alkyl esters and the use of alkali metal alcoholate catalysts leads to products with a very high cloud point, it has surprisingly been found that the addition of alkylene glycols to these catalysts significantly improves activity and/or selectivity. However, the use of the system according to the invention of homogeneous catalyst and co-catalyst surprisingly leads to alkoxylated alkyl esters which have a hydroxyl value near the theoretical value and which are distinguished by a very low cloud point.

Fatty acid alkyl esters

The fatty acid alkyl esters used as starting materials are derived from saturated and/or unsaturated fatty acids containing 6 to 22 and preferably 12 to 18 carbon atoms and alcohols containing 1 to 22 and preferably 1 to 4 carbon atoms. Typical examples are methyl, ethyl, propyl, butyl and/or stearyl esters of caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils or in the reduction of aldehydes from Roelen's oxosynthesis. Cocofatty acid and/or tallow fatty acid methyl esters are preferably used as starting materials.

Catalysts

Catalyst component (a) may be selected from alkali metal hydroxides, alkaline earth metal hydroxides, alkali metal alcoholates and/or alkaline earth metal alcoholates. Typical examples are sodium hydroxide, potassium hydroxide, magnesium hydroxide, calcium hydroxide, barium hydroxide, sodium methylate, potassium tert.butylate, calcium ethylate and/or magnesium methylate. Potassium hydroxide and/or sodium methylate is/are preferably used. The catalysts (a) are used in quantities of normally 0.1 to 1.5% by weight and preferably 0.4 to 1% by weight, based on the end products.

Catalyst component (b), i.e. the co-catalyst, may be selected from alkylene glycols containing 2 to 6 carbon atoms, for example ethylene glycol, diethylene glycol, propylene glycol and/or dipropylene glycol. The co-catalysts are used in quantities of normally 0.5 to 5% by weight and preferably 1 to 4% by weight, based on the end products.

Alkoxylation

The alkoxylation reaction may be carried out in known manner. To this end, the alkyl ester is normally introduced into a stirrer-equipped autoclave and the homogeneous catalyst is subsequently added, for example in the form of a solution in water, but preferably in methanol. It has proved to be of advantage to purge the autoclave thoroughly with nitrogen before the reaction to remove all traces of atmospheric oxygen and to remove methanol used as solvent by evacuation. The autoclave is then heated. The alkoxylation reaction is carried out at temperatures of preferably 140 to 180° C. and more preferably 160 to 170° C. The alkylene oxide, which may be ethylene oxide, propylene oxide or mixtures of both, is introduced into the reactor by a siphon. The autogenous pressure can rise to about 5 bar. The alkylene oxide, preferably ethylene oxide, is preferably used in a quantity of on average 1 to 20 moles and more preferably 8 to 15 moles per mole of alkyl ester. The addition of the alkylene oxide is statistical, i.e. the insertion is not a highly selective reaction in which 1 mole of fatty acid alkyl ester reacts with exactly n moles of alkylene oxide. Instead, a complex mixture of esters alkoxylated to different degrees is obtained. The reaction is over when the pressure in the reactor falls to about 0.5 bar. For safety reasons, it is advisable to stir the mixture for another 30 minutes before the reactor is cooled and vented. If desired, the alkaline catalyst can be neutralized by the addition of acids, for example phosphoric acid, acetic acid, lactic acid or the like.

COMMERCIAL APPLICATIONS

The alkoxylated fatty acid alkyl esters obtainable by the process according to the invention have hydroxyl values near the theoretical value and are distinguished by comparatively low cloud points. Accordingly, in relation to known comparable products which have been obtained using other catalysts, optimal washing performance is achieved at lower temperatures.

EXAMPLES

General procedure. 256 g (1 mole) of technical $C_{12/16}$ cocofatty acid methyl ester were introduced into a 1-liter stirred autoclave and the proposed quantity of catalyst in the form of a solution in methanol (ca. 30% by weight) was added. The autoclave was closed and then alternately purged with nitrogen and evacuated three times to rule out the presence of atmospheric oxygen and to remove the methanol solvent. The reaction mixture was then heated to 165° C. under a nitrogen blanket and 484 g (11 moles) of ethylene oxide were introduced in portions, the autogenous pressure initially rising to 3.5 bar. The reaction was continued until the pressure had fallen to 0.5 bar. After stirring for another 30 minutes, the autoclave was cooled and vented.

The results of the tests are set out in Table 1. The quantities of catalysts used are based on the end product. The theoretical hydroxyl value was 23.2.

TABLE 1

Ethoxylation of cocofatty acid methyl ester

| Ex. | Catalyst | [Cat.] % by wt. | Co-catalyst | [Co-cat.] % by wt. | S.V. | OH V. | Cl. P. ° C. |
|---|---|---|---|---|---|---|---|
| 1 | Potassium hydroxide | 0.4 | Ethylene glycol | 3.8 | 77.4 | 29.3 | 53.0 |
| C1 | Calc. hydrotalcite | 1.0 | None | — | 79.4 | 6.4 | 64.5 |
| C2 | Potassium hydroxide | 1.0 | None | — | * | * | * |
| C3 | Potassium hydroxide | 1.0 | Lauric acid | 0.5 | * | * | * |
| C4 | Sodium methylate | 1.2 | None | — | 73.1 | 21.2 | 6.0 |
| C5 | Sodium methylate | 0.8 | Methoxy ethanol | 0.33 | 75.4 | 14.7 | 70.5 |

Legend:
S.V. = Saponification value
OH V. = OH value
Cl. P = Cloud point
* = No reaction

We claim:
1. A process for making alkoxylated fatty acid alkyl esters corresponding to formula

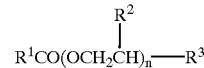

wherein $R^1CO$ is a linear or branched acyl group containing from 6 to 22 carbon atoms and up to 3 double bonds, $R^2$ is hydrogen or a methyl group, $R^3$ is a linear or branched alkyl group containing from 1 to 22 carbon atoms and n is a number of from 1 to 20, the process comprising:

(a) providing a fatty acid alkyl ester;
(b) providing an alkylene oxide component;
(c) providing a catalyst component containing a mixture of:
   (i) a primary catalyst selected from the group consisting of an alkali metal hydroxide, an alkaline earth metal hydroxide, an alkali metal alcoholate, an alkaline earth metal alcoholate and mixtures thereof; and
   (ii) an alkylene glycol having from 2 to 6 carbon atoms; and
(d) reacting (a)–(c) to make the alkoxylated fatty acid alkyl ester.

2. The process of claim 1 wherein the primary catalyst is employed in a quantity of from 0.1 to 1.5% by weight, based on the weight of the alkoxylated fatty acid alkyl ester.

3. The process of claim 1 wherein the primary catalyst is employed in a quantity of from 0.4 to 1.0% by weight, based on the weight of the alkoxylated fatty acid alkyl ester.

4. The process of claim 1 wherein the alkylene glycol is employed in a quantity of from 0.5 to 5% by weight, based on the weight of the alkoxylated fatty acid alkyl ester.

5. The process of claim 1 wherein the alkylene glycol is employed in a quantity of from 1 to 4% by weight, based on the weight of the alkoxylated fatty acid alkyl ester.

6. The process of claim 1 wherein the reaction is carried out at a temperature of from 140 to 180° C.

7. The process of claim 1 wherein the alkylene oxide component is ethylene oxide.

8. The process of claim 1 wherein the alkylene oxide component is employed in a quantity of from 1–20 moles of alkylene oxide per mole of alkyl ester.

* * * * *